United States Patent [19]

Kobayashi et al.

[11] Patent Number: 5,594,548
[45] Date of Patent: Jan. 14, 1997

[54] IN-FURNACE INSPECTION MACHINE UTILIZING A DOUBLE-WALLED STRUCTURE

[75] Inventors: Hiroaki Kobayashi; Hiroshi Igarashi, both of Hitachinaka; Junichi Adachi, Kashiwa; Shinichi Usui, Tokyo-To; Shunji Yoshizawa, Yokohama; Hirotaka Uehara, Noda, all of Japan

[73] Assignees: Kawasaki Jukogyo Kabushiki Kaisha, Hyogo-Ken; Doryokuro Kakunenryo Kaihatsu Jigyodan, Tokyo-To, both of Japan

[21] Appl. No.: 462,279

[22] Filed: Jun. 5, 1995

[30] Foreign Application Priority Data

Jun. 7, 1994 [JP] Japan ................. 6-125269

[51] Int. Cl.⁶ ............................................. G01B 11/24
[52] U.S. Cl. ......................... 356/376; 356/241; 356/381
[58] Field of Search ........................ 356/241, 376, 356/381, 384

[56] References Cited

U.S. PATENT DOCUMENTS

| 4,508,448 | 4/1985 | Scholdstrom et al. | 356/5 |
| 4,708,482 | 11/1987 | Netheisel | 356/376 |
| 5,127,736 | 7/1992 | Neiheisel | 356/376 |
| 5,223,908 | 6/1993 | Scott et al. | 356/381 |

Primary Examiner—Richard A. Rosenberger
Assistant Examiner—Robert Kim
Attorney, Agent, or Firm—Oliff & Berridge

[57] ABSTRACT

A machine for inspecting the surface conditions of structural members within a furnace, particularly within a furnace operating at a high temperature or with a highly radioactive environment, such as a melting furnace for processing radioactive wastes. The machine comprises a laser-transmission optical fiber incorporated with a laser projector at one end thereof inserted into the furnace and being connected to a laser beam source outside the furnace; a fiberscope incorporated with the objective portion at one end thereof inserted into the furnace and being connected to an image sensor located outside the furnace; means for calculating the distance to a structural wall surface on which the laser beam from a tip portion of the inspection machine has fallen, by subjecting an image from the image sensor to image processing; a double-walled tube of a structure such that the laser-transmission optical fiber is incorporated through an inner tube thereof, and a coolant introduced into a passageway within the inner tube returns in the vicinity of the laser projector at the tip portion; and a double-walled tube of a structure such that the fiberscope is incorporated through an inner tube thereof, and a coolant introduced into a passageway within the inner tube returns in the vicinity of the objective portion at the tip portion.

5 Claims, 6 Drawing Sheets

IN-FURNACE INSPECTION MACHINE UTILIZING A DOUBLE-WALLED STRUCTURE

BACKGROUND OF THE INVENTION

The present invention relates to a machine for inspecting the surface conditions of structural members within a furnace, particularly inside a furnace operating at a high temperature and/or with a highly radioactive environment, such as a melting furnace for radioactive wastes processing.

A view of the configuration of an inspection machine inside a vacuum chamber that was disclosed in Japanese Patent Laid-Open Publication No. Sho 60-169745 is shown in FIG. 6 as an example of the prior-art. In this prior-art, an image fiber 106 is used instead of an industrial television camera in a vacuum chamber 101 of a melting device. An arm tip part 105 capable of changing its protruding direction is attached to a lower end of a main arm portion 104 capable of moving up and down in an axial direction of a tubular structural member 103. Movable blocks capable of adjusting in the length are suspended from the arm tip portion 105, and an objective part 102 of the image fiber is mounted thereon.

This configuration is capable of withstanding a temperature of approximately 250° C. within the vacuum chamber 101 and makes it unnecessary to provide the large cooling gas that would be needed if an industrial television camera system was inserted. Thus it provides an inspection machine that is far superior from the viewpoints of heat resistance, monitoring range, and ease of maintenance.

The above described prior-art made it possible to continuously monitor the interior of a vacuum chamber without requiring the use of large quantity of coolant for cooling, by using imaging portion of an image fiber that can withstand a temperature of approximately 250° C. instead of an industrial television camera that can withstand a temperature of only about 60° C., which had been used up until that time.

However, there are certain problems with the above described prior-art, as described below. The first problem concerns the inspection-hostile environment. When the object being inspected is a melting furnace for radioactive wastes processing or the like, the decay heat due to the high level of residual radioactivity can cause the interior of the furnace to reach a fairly high temperature of 400° C. to 500° C. However, the thermal resistance of the fiberscope is only about 250° C., so it cannot be used without some form of cooling machine.

Further, since the various drive mechanisms of the inspection machine inserted into the furnace are exposed to high levels of radioactivity in addition to high temperatures, the components thereof have extremely short lifetimes and thus it is necessary to replace them after a short period of time. However, the inside of the melting furnace is a highly radioactive region, called a hot cell, so that this replacement of components must be performed by remote operation, and thus there are extreme restrictions on use.

Another problem concerns inspection method. Quantitative inspection is essential for purposes such as lifetime estimation, but the above described prior-art cannot be used for such purposes because it provides qualitative inspection by observation.

SUMMARY OF THE INVENTION

The present invention was devised in the light of the above described problems with the prior art, and its objective is the provision of an inspection machine that has superior thermal and radiation resistances but a simple configuration and low fabrication costs; provides a highly accurate, quantitative measurement of the surface conditions of structural members inside a furnace; and also enables qualitative inspection by direct observation.

The above objective is achieved by an in-furnace inspection machine as laid out in the claims of the present invention.

In other words, a first aspect of the present invention provides an in-furnace inspection machine comprising a laser-transmission optical fiber incorporated with a laser projector at one end thereof inserted into the furnace and being connected to a laser beam source outside the furnace; a fiberscope incorporated with the objective portion at one end thereof inserted into the furnace, the objective portion being arranged in such a manner as to be capable of observing an irradiated point on a structural wall surface inside the furnace onto which light projected from the laser projector falls, and being connected to an image sensor located outside the furnace; means for calculating the distance to the structural wall surface on which the laser beam from a tip portion of the inspection machine has fallen, by subjecting an image from the image sensor to image processing; a double-walled tube of a structure such that the laser-transmission optical fiber is incorporated through an inner tube thereof, and a coolant introduced from a supply port outside the furnace into a passageway within the inner tube turns in the vicinity of the laser projector at the tip portion and flows back through a gap between the inner tube and an outer tube thereof to an outflow port outside the furnace; and a double-walled tube of a structure such that the fiberscope is incorporated through an inner tube thereof, and a coolant introduced from a supply port outside the furnace into a passageway within the inner tube turns in the vicinity of the objective portion at the tip portion and flows back through a gap between the inner tube and an outer tube thereof to the outflow port outside the furnace; wherein the double-walled tube accommodating the laser-transmission optical fiber and the double-walled tube accommodating the fiberscope are incorporated in a drive shaft provided with means for obtaining straight-line motion in an axial direction and means for obtaining rotational motion in a circumferential direction, and a portion below a lower end portion of the drive shaft is provided by a structure whereby the positional relationship between the laser projector of the double-walled tube accommodating the laser-transmission optical fiber and the objective portion of the double-walled tube accommodating the fiberscope is fixed; the drive portions of the drive shaft, external surfaces of the double-walled tube accommodating the laser-transmission optical fiber and the double-walled tube accommodating the fiberscope protruding from a lower end portion of the drive shaft, and penetration portions of the drive shaft through a case of the inspection machine have an airtight configuration; and surface shape of structural members inside the furnace are determined from distance data obtained by continuously scanning the laser beam over the surfaces.

In a second aspect of the present invention, the projected laser beam of the above described machine is either a spot-shaped beam or a slit-shaped beam forming a vertical surface, wherein the light axis of the spot-shaped beam or the plane formed by the slit-shaped beam passes through the center of rotation of said drive shaft.

In a third aspect of the present invention, the fiberscope is incorporated with an irradiating light projector at an end thereof inside the furnace and is configured integrally with a light guide (an optical fiber for transmitting irradiating light) connected to an irradiating light source arranged outside the furnace.

In a fourth aspect of the present invention, at least one assembly of a laser transmitting and projecting system and an image receiving and transmitting system is provided.

The operation of the in-furnace inspection machine in accordance with the present invention will be described below with reference to a preferred embodiment thereof.

DESCRIPTION OF THE PREFERRED EMBODIMENT

Figure 1:
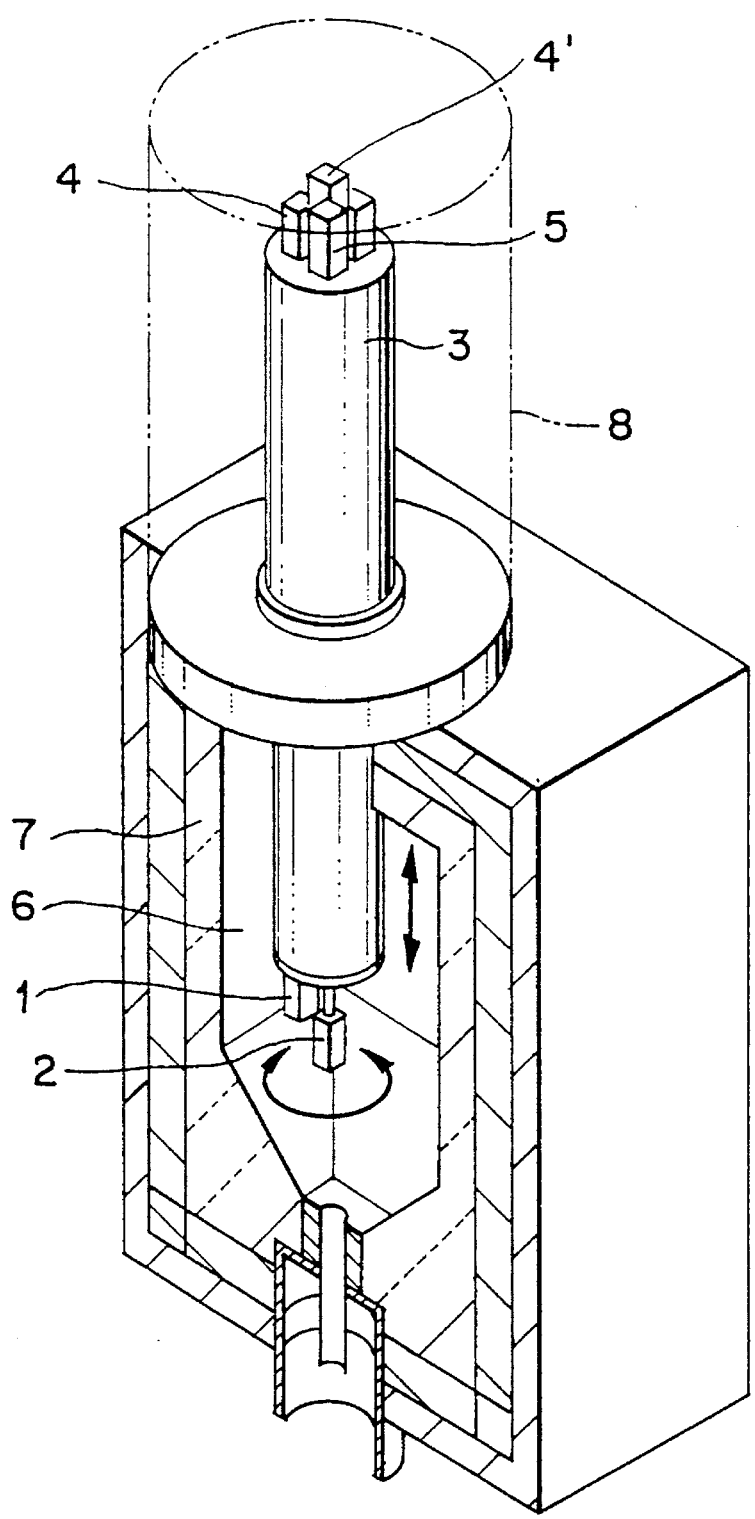
FIG. 1 is a perspective external view of an in-furnace inspection machine based on the present invention.
Figure 2:
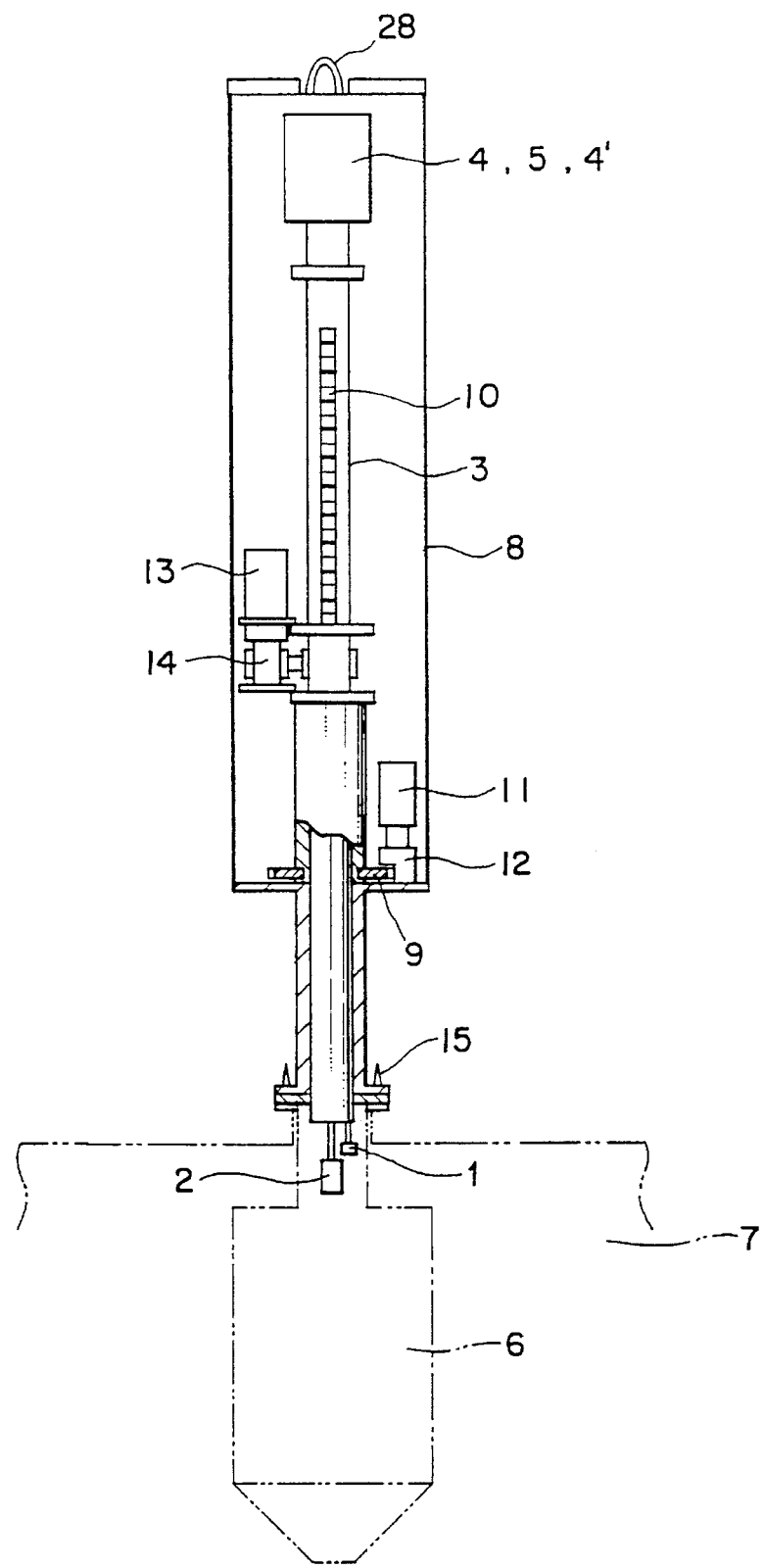
FIG. 2 is an abbreviated lateral cross-sectional view through the in-furnace inspection machine of FIG. 1.
Figure 3:
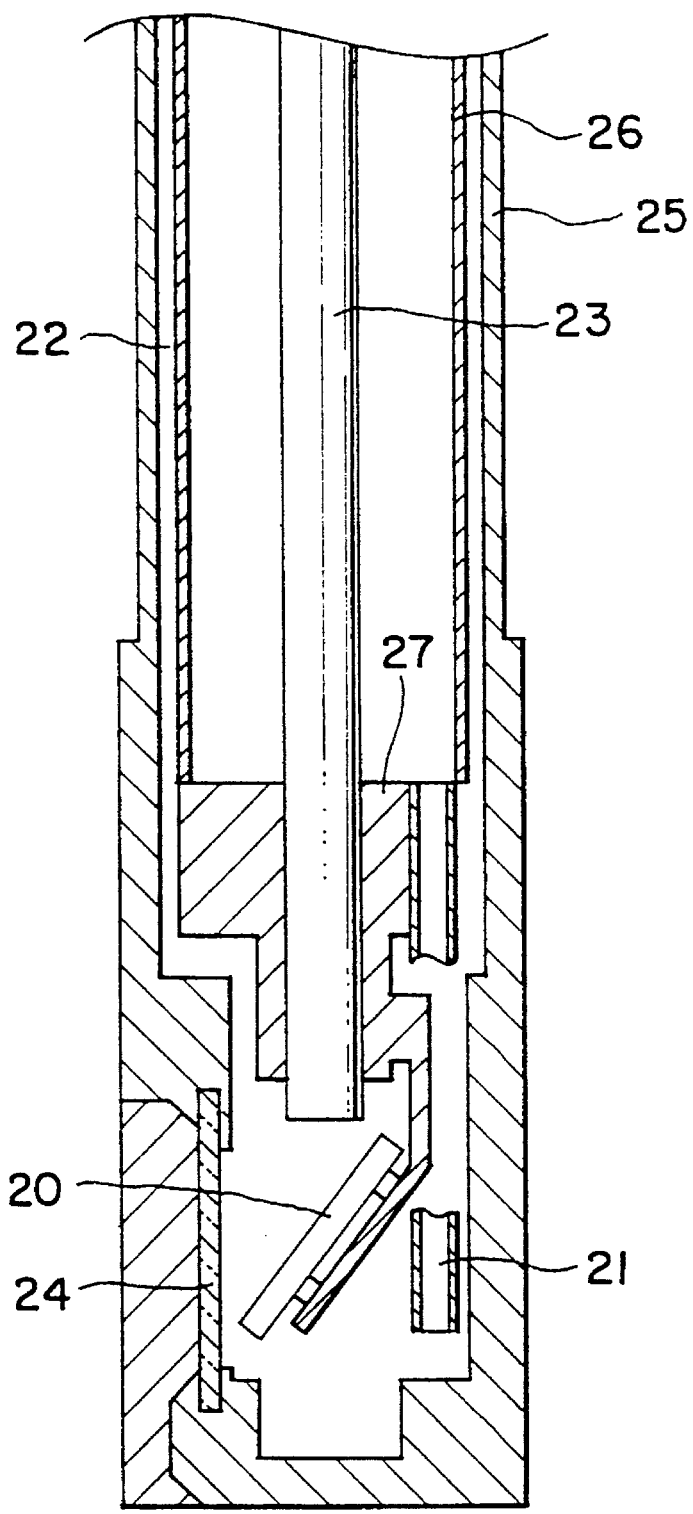
FIG. 3 is a partial expanded cross-sectional view of the objective portion of FIG. 2.

An embodiment of the in-furnace inspection machine in accordance with the present invention is shown in FIGS. 1 to 3. This machine is directed to a glass melting furnace which is one type of installation for processing highly radioactive wastes and which uses a method of solidifying the radioactive wastes for volume reduction and also place it in in a stable and easy-to-handle form, then solidifies it together with glass material, to enable long-term storage. Since this glass melting furnace is operated at a high temperature, the inside surfaces of a metal casing thereof that come into contact with the molten glass are protected by refractory members, but these refractory members are expected to be corroded after a few years of service. For that reason, it is necessary to inspect the conditions inside the melting furnace regularly during the service period, and thus verify the integrity of the melting furnace as well as determine the lifetime of the melting furnace in a systematic manner. The present invention relates to an inspection machine for performing this periodic inspection for corrosion damage of the interior of the furnace.

Figure 4:
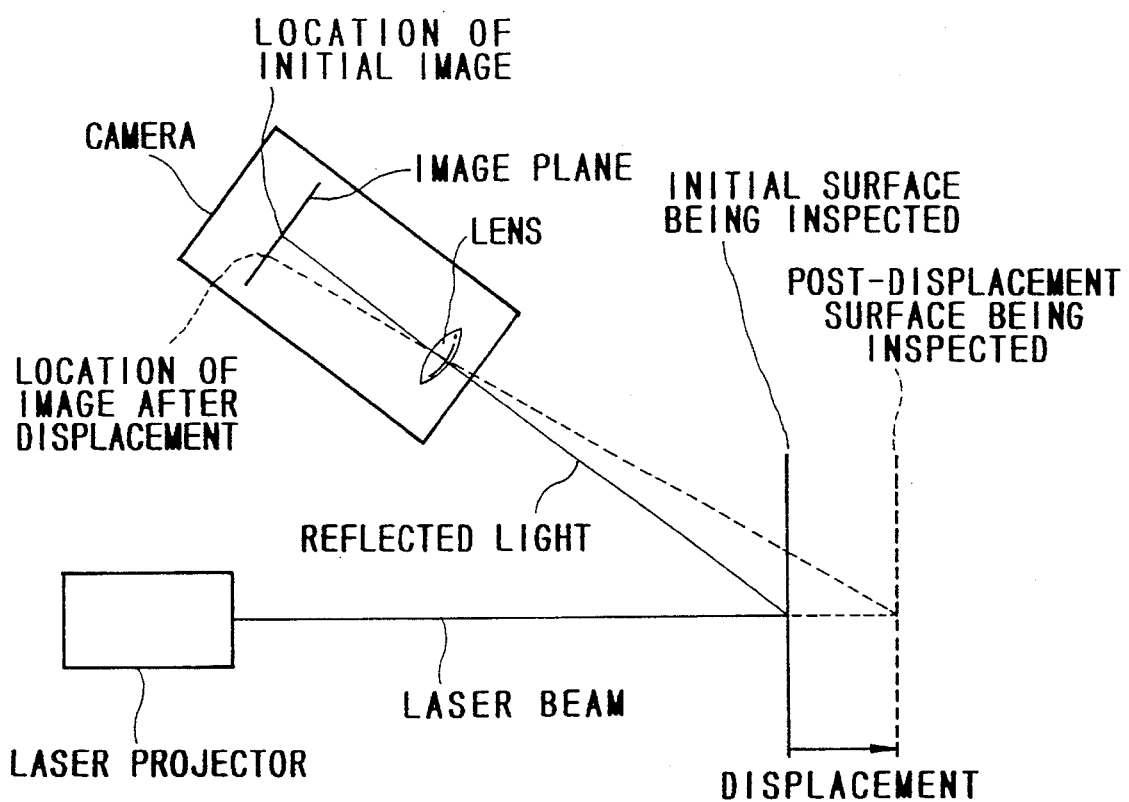
FIG. 4 is a view illustrative of the basic concept of distance measurement by triangulation.
Figure 5:
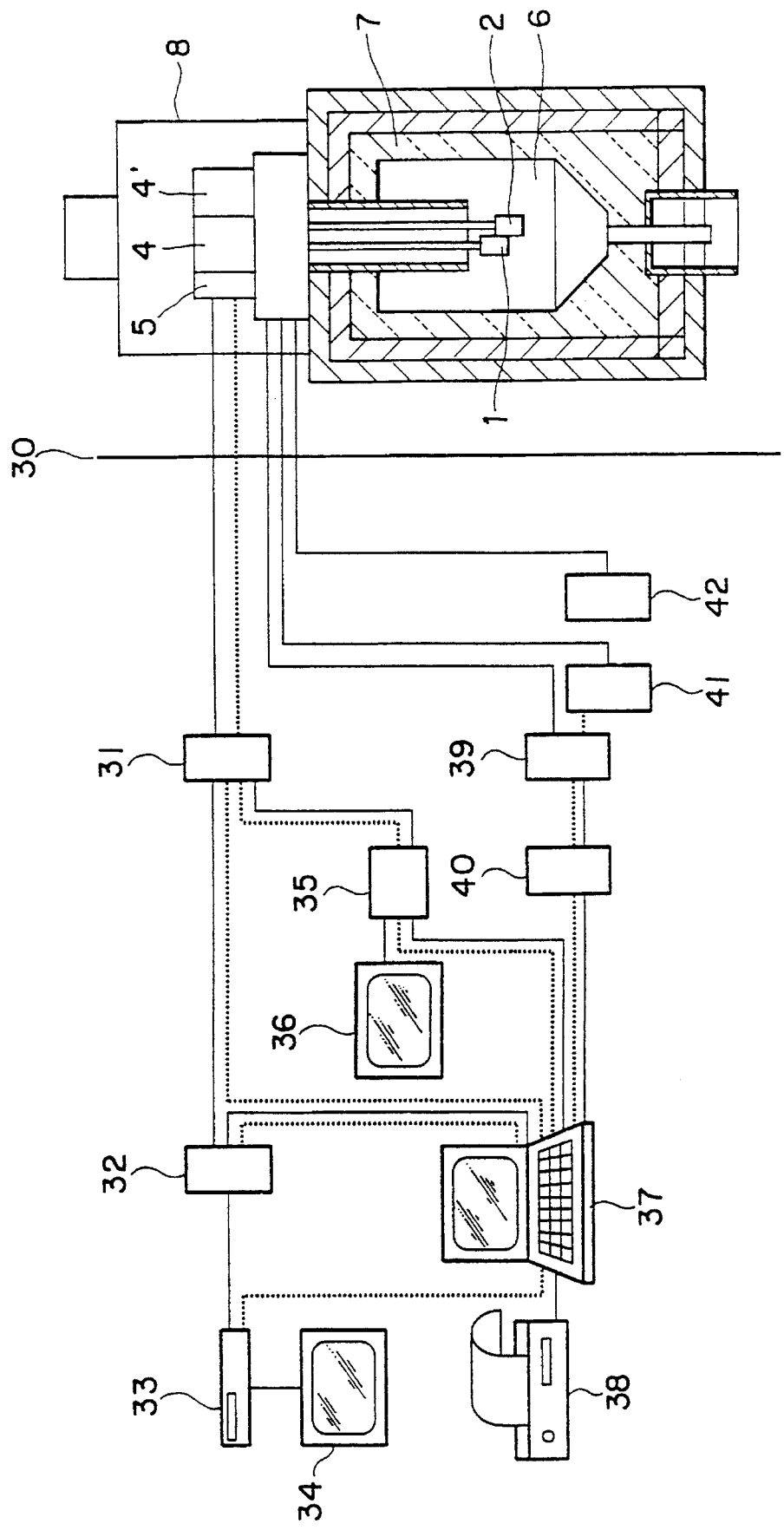
FIG. 5 is a view of an example of the overall system configuration when using the in-furnace inspection machine of the present invention to inspect the walls of structural members inside a furnace.
Figure 6:
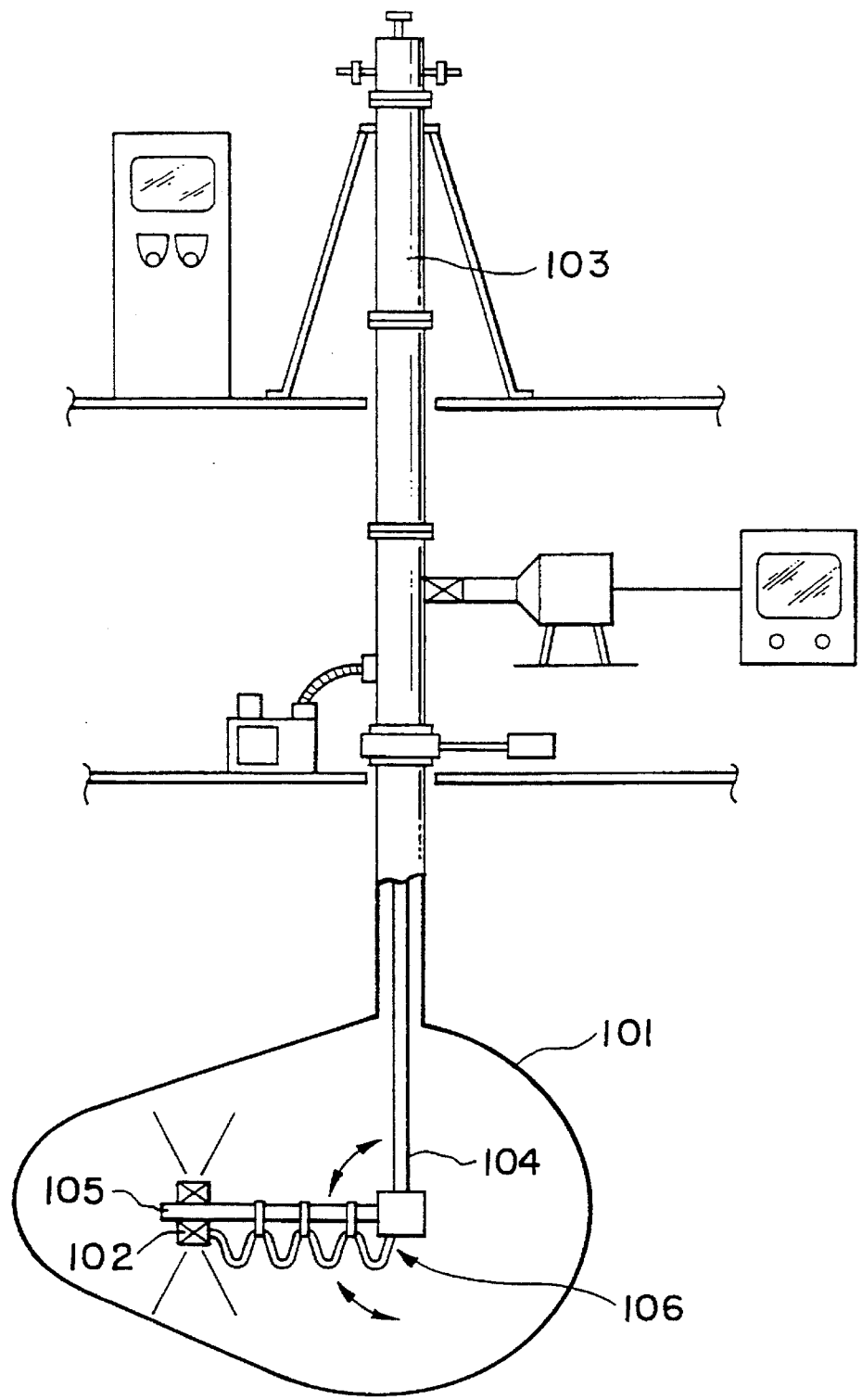
FIG. 6 is a view of an example of the prior art.

A perspective view of the exterior of this in-furnace inspection machine is shown in FIG. 1, an abbreviated lateral cross-sectional view through this in-furnace inspection machine is shown in FIG. 2, and a partial expanded cross-sectional view of the objective portion of FIG. 2 is shown in FIG. 3. In addition, a view illustrative of the basic concept of distance measurement by triangulation is shown in FIG. 4 and an example of the overall system configuration when using the in-furnace inspection machine of the present invention to inspect the walls inside a furnace is shown in FIG. 5.

In FIGS. 1 to 5: reference number 1 denotes a laser projector, 2 denotes an objective portion, 3 denotes an elevational shaft, 4 denotes a laser source, 5 denotes a television camera, 6 denotes a furnace, 7 denotes a refractory member, 8 denotes a protective cover for a drive mechanism, 9 denotes a rotational gear wheel, 10 denotes a rack-and-pinion mechanism, 11 and 13 denote electric motors, 12 and 14 denote speed reducers, 15 denotes a guide pin, 20 denotes a mirror, 21 denotes an inlet pipe for a coolant, 22 denotes an outlet passage for the coolant, 23 denotes a fiberscope, 24 denotes a glass window pane, 25 denotes an outer tube, 26 denotes an inner tube, 27 denotes a support bracket, 30 denotes a cell wall, 31 denotes a switcher, 32 denotes a video *teroppa*, 33 denotes a video tape deck, 34 and 36 denote monitor television sets, 35 denotes a image processor, 37 denotes a personal computer, 38 denotes a printer, 39 denotes a servo amplifier, 40 denotes a servo controller, 41 denotes an interlock circuit, and 42 denotes a thermometer.

One end of an optical fiber for transmitting laser light is connected to the laser source 4 and the other end is connected to the laser projector 1. One end of the fiberscope 23 is connected to the television camera 5 and the other end is connected to the objective portion 2. Note that the description of this embodiment relates to a system in which a television camera is used as means for converting an optical image into an electrical signal, and this means is referred to as "television camera" herein, although it should be obvious to those skilled in the art that this means is not limited thereto.

The laser-transmission optical fiber and the fiberscope are each passed through a tube of a double-walled configuration. The interior of the inner tube 26 of each of these double-walled tubes acts as a passage for a low-temperature coolant, and a space between each outer tube 25 and the corresponding inner tube 26 acts as a passage for coolant whose temperature has been raised by heat transferred from the outer tube 25 side when the machine is inserted into the high-temperature furnace 6. The double-walled tube for the light-emitting optical fiber and the double-walled tube for the light-receiving optical fiber are combined together and pass through the elevational shaft 3.

Each fiber-accommodating tube is airtightly sealed at a lower through portion of the elevational shaft 3.

A partial expanded cross-sectional view of the objective portion 2 is shown in FIG. 3. The fiberscope 23 is passed through the center of the inner tube 26 and the lower end portion thereof is supported by the support bracket 27 which is fixed to the lower end portion of the inner tube 26. A lower end surface of the fiberscope 23 faces the mirror 20 which reflects the conditions within the furnace being inspected, through the glass window pane 24. An image of the interior of the furnace 6 is transmitted to the television camera 5 provided in an upper portion.

As shown in FIG. 3, the objective portion 2 has a configuration that is completely isolated from the outer environment. The low-temperature coolant (usually air) flowing downward through the central portion of the double-walled tube enters the objective portion 2 where the mirror 20 and other components are provided, through the coolant inlet pipe 21. After cooling the mirror 20, the glass window pane 24, and the lower end surface of the fiberscope 23, the coolant flows upward and out through the coolant passage 22 formed by the space between the outer tube 25 and the inner tube 26. This ensures that the mechanisms inside the objective portion 2, as well as the other components such as the fiberscope 23 located thereabove, are not affected by the high-temperature atmosphere inside the furnace 6.

The portions of the in-furnace inspection machine in accordance with the present invention that are inserted into the furnace are completely enclosed inside the elevational shaft 3 and are not provided with any driven (dynamic) parts. In other words, both the laser projector 1 and the objective portion 2 protruding from the lower portion of the elevational shaft 3 are fixed to the elevational shaft 3, and the height or angle of the laser projector 1 and the objective portion 2 inside the furnace 6 can be set when the condition of the refractory member 7 inside the furnace 6 is being inspected, by causing the elevational shaft 3 itself to be raised/lowered or rotated by the drive mechanisms accommodated inside the protective cover 8 for the drive mechanism which is arranged at a position above the elevational shaft 3 where it is not affected by the furnace 6.

To raise or lower the elevational shaft 3, the electric motor 13 is driven so that a gear wheel (not shown) engaged with the rack-and-pinion mechanism 10 is driven via the speed reducer 14, and thus the assembly is raised or lowered. Similarly, to rotate the elevational shaft 3, the electric motor 11 is driven so that a gear wheel (not shown) engaged with the rotational gear wheel 9 is driven via the speed reducer 12, and thus the assembly is rotated to any desired angle. This makes it possible for the laser projector 1 and the objective portion 2 to always operate safely over a long period of inspection time, while inserted in a high-temperature or highly radioactive environment.

The basic concept of distance measurement by triangulation, which is used by the in-furnace inspection machine of the present invention, is shown in FIG. 4. In this figure, if a laser beam is projected onto a surface that is the object being inspected and the light reflected from the surface being inspected is watched by a television camera, the location of the bright spot point the image plane of the camera will change with the distance to the surface being inspected. Thus it is clear that the distance to the surface being inspected can be calculated by processing the image of the area location obtained during measurement, after calibrating the machine by measuring the distance from the inspection machine to various objects at distances that are previously known, thus obtaining the relationships between the locations of light spot on the image plane of the camera and the corresponding distances.

In practice, the laser beam generated from the laser source 4 is shone as a spot laser beam from the laser projector 1 through the laser-transmission optical fiber and onto various different refractory members 7 affixed inside the furnace 6. The reflected light thereof is transmitted from the mirror 20 provided in the objective portion 2, through the fiberscope 23, and to the television camera 5 provided on an upper portion of the elevational shaft 3, and the location of the surface on which it shines is determined to be the initial spot location on the image plane. The distance data obtained from the television image signal of the area inside the furnace 6 that is watched by the television camera 5 is sent to a data processing device that is located in an area separated from the hot cell by the cell wall, in an environment that is completely unaffected by radiation.

The concept used for the measurement of a change in distance of a certain point on the light axis, if the position of the object being inspected has displaced along the light axis of the spot beam, is shown in FIG. 4. The inspection machine of the present invention is used for measuring surface conditions, such as those of refractory members inside a melting furnace that are changed by corrosion. An outline of measurement by a spot beam is described below.

First of all, the drive shaft is moved in such a manner that the laser spot beam is repeatedly moved slightly at a predetermined pitch in both the axial direction and the circumferential direction along the surface of the object being inspected, then stopped, so that the entire surface being inspected is scanned by the laser beam. Each time the drive shaft is stopped, the laser beam emitted at that position from the laser source, which is provided outside the furnace, is incident on the light-admitting portion of the laser-transmission optical fiber through a focussing lens. The incident light bundle that is transmitted into the fiber is projected from the projector onto the object being inspected inside the furnace. The bright spot generated thereby on the object being inspected is accepted by the objective portion of the fiberscope, is transmitted through the fiber, and is imaged on the image plane of the television camera provided outside the furnace. This enables measurement of the bright spot, or rather, of the distance to the object being inspected.

The scan pitch of the above measurements and the measured distance data can be used to model the surface conditions, by processing over the measurement range performed by the data processing device that is located in a position separated from the hot cell by the cell wall, in an environment that is completely unaffected by high levels of temperature and radiation within the furnace.

The above description concerned a spot-shaped beam, but a slit-shaped beam could equally well be used. In such a case, the distances to all the points on a line on the surface of the object being inspected at which the slit-shaped beam is incident can be measured at the same time. This means that the surface conditions can be modeled by repeating the measurements at a constant pitch in the direction perpendicular to the plane of the slit-shaped beam, then processing the thus-obtained data in a manner similar to that used for a spot-shaped beam. It should be noted, however, that if the range to be inspected exceeds the length of the slit-shaped beam within the television camera, scanning in the direction perpendicular to the plane of the slit-shaped beam and in the direction of the slit-shaped beam is repeated until the entire region being inspected has been covered.

To ensure that measured values are reproducible when the inspection machine of this invention is used to measure the same locations, it is necessary to ensure that the inspection machine is installed accurately at fixed locations with respect to the furnace. With a glass melting furnace for solidifying high-level radioactive wastes, it is inevitable that this installation work must be done by remote operation, because of the high levels of radioactivity inside the furnace, not only while it is in operation, but also when it is halted for overhaul. One method of ensuring repeatability of the positioning of the in-furnace inspection machine could be to use the guide pin 15 as a reference point for mounting the in-furnace inspection machine on an upper portion of the furnace 6 by remote-control manipulation.

The description now turns to a brief outline of the measurement of amounts of corrosion in refractory members 7 affixed inside the furnace 6. First of all, the various distances to the walls of the furnace are measured while the furnace 6 is being constructed. Measurements are then taken at fixed periods during operation, at the same locations on the surfaces of the refractory members 7 as those measured during construction, after use at high temperatures or in a highly radioactive environment. If there should be any displacement due to corrosion of the surface of a refractory member 7, the measured value of the distance will change, and a comparison of the two values can be used to provide accurate, quantitative calculation of the corrosion loss of each refractory member 7.

The above description dealt with a method of measuring corrosion loss of a refractory member 7 by comparing an initial measurement obtained for each measurement point during the construction of the furnace with a measurement obtained after a fixed period of service. In the furnace 6 is a glass melting furnace, however, there will be virtually no corrosion above a standard operating liquid level of the melted glass, so it is also possible to quantitatively measure corrosion losses in the refractory members 7 by comparing a location on the surface of a refractory member 7 of the furnace 6 with a location on the surface of the refractory member 7 that is below the upper surface of the melted glass.

If the bottom of the furnace 6 is hopper shaped, as shown in FIGS. 1 and 2, one assembly of the laser projector 1 and objective portion 2 will be unable to measure all the changes in the wall surfaces, because the manner in which each component is fixed makes it inevitable that some locations on the wall surfaces irradiated by the laser beam will be outside the field of view of the television camera. To allow for these blindspots, the present invention also provides a plurality of assemblies, each comprising a laser projector 1 and a objective portion 2 and having different angles formed between the laser beam and reflected beam thereof, and all passing through the elevational shaft 3. With this configuration the most suitable assembly can be selected to suit the distance between each object being inspected and the inspection machine.

Since a machine based on the present invention incorporates an irradiation-transmitting optical fiber inside the fiberscope, inspection by visual observation can also be provided by irradiating the interior of the furnace.

If the irradiating laser beam used when measuring distances by the triangulation method is made to be a spot-shaped beam or a slit-shaped beam, calculation of the distance to the object being inspected along the light axis of the spot-shaped beam or in the plane of the slit-shaped beam is simple for image processing. In addition, when measuring a physical surface shape by the inspection machine, the data processing is simpler by means of measuring from an immovable point acting as a reference. Therefore, if the laser beam is made to be either a spot-shaped beam or a slit-shaped beam forming a vertical surface, it is preferable to rotate the light axis of the spot-shaped beam or the plane of the slit-shaped beam about the rotational center and thus make this rotational center a Z-axis in a cylindrical coordinates system of three-dimensional positional measurement data. For that reason, calculations of distances or surface shape can be performed simply and precisely by making the laser beam to be either a spot-shaped beam or a slit-shaped beam and locating the light axis of the spot-shaped beam or the plane of the slit-shaped beam through the center of rotation of the drive shaft.

The above description stated that the laser beam projected from the laser projector is either a spot-shaped beam or a slit-shaped beam, but the inside surfaces of the glass melting furnace to which the present invention is directed are covered with black glass and hence the reflectivity thereof is extremely low. Therefore, if the laser beam has a slit shape, the light energy density (light strength) of the beam is low and virtually none of it is reflected. In contrast, it is possible to increase the light energy density of a spot-shaped beam, and thus it is possible to measure distances to the surfaces of structural members within a glass melting furnace with such a laser beam.

As should be clear from the above description of this embodiment, the present invention provides the following effects:

1) Since the only portions inserted into the furnace are the optical fiber and its associated components, it is possible to ensure a high degree of thermal resistance with a comparatively simple cooling mechanism because the optical fiber itself has a certain amount of thermal resistance in addition to a superior radiation resistance.

2) Configuring the inspection head of static devices alone, with no movable components such as bearings, increases reliability and removes the need for maintenance during use. The high sealing performance also enables easy and safe maintenance with a directed operation by decontaminating the head portion by means such as high-pressure water after the inspection is completed.

3) Use of optical fibers not only makes it possible to reduce the size of portions inserted into the furnace, but it also enables the inspection of furnaces through restricted openings such as ports or ducts.

4) Quantitative measurements of the corrosion of surfaces of structural members inside a furnace make it possible to estimate lifetimes.

5) The incorporation of the light-transmission optical fiber and the fiberscope into a single assembly makes it possible to perform visual, qualitative observation in addition to quantitative measurement of corrosion, without having any effect on the size and form of the portions inserted in the furnace.

6) The transmission of images using optical fibers makes it possible to obtain clear pictures at only a fraction of the power required for measuring instruments that use periscopes, when the transmission distance is long.

7) Forming the laser beam into a spot-shaped or a slit-shaped beam that defines a vertical surface makes it possible to easily obtain concise and precise measurement or calculation of surface shape, by passing the light axis of the spot-shaped beam or the plane of the slit-shaped beam through the rotational center, thus making this rotational center a Z-axis in a cylindrical coordinate system of three-dimensional positional measurement data.

What is claimed is:

1. An in-furnace inspection machine for the interior of a furnace, comprising a light-projecting portion and an objective portion inserted into a furnace that contains a high-temperature, highly radioactive atmosphere; a light-source and an imaging portion located outside said furnace; means for connecting portions inside said furnace to portions outside said furnace; a main inspection machine portion having means for freely raising, lowering, and rotating all of said portions as a single assembly; and a data processing device located outside a hot cell through a cell wall, said in-furnace inspection machine comprises:

a laser-transmission optical fiber incorporated with a laser beam projector at one end thereof inserted into said furnace and being connected to a laser source at the other end thereof outside said furnace;

a fiberscope incorporated with said objective portion at one end thereof inserted into said furnace, said objective portion being arranged so as to be capable of observing an irradiated point on a structural wall surface inside said furnace onto which laser light projected from said laser projector falls, and being connected to an image sensor located at the other end of the fiberscope outside said furnace;

means for calculating the distance from a tip portion of said inspection machine to said structural wall surface on which said laser beam has fallen, by processing an image signal from said image sensor;

a double-walled tube of a structure such that said laser-transmission optical fiber is incorporated inside an inner tube thereof, and a coolant introduced from a supply port outside said furnace into a passageway within said inner tube turns in the vicinity of said laser projector at said tip portion and flows back through a gap between said inner tube and an outer tube thereof to an outflow port outside said furnace; and a double-walled tube of a structure such that said fiberscope is incorporated inside an inner tube thereof, and a coolant introduced from a supply port outside said furnace into a passageway inside said inner tube turns in the vicinity of said objective portion at said tip portion and flows back through a gap between said inner tube and an outer tube thereof to the outflow port outside said furnace; wherein:

said double-walled tube accommodating said laser-transmission optical fiber and said double-walled tube accommodating said fiberscope are incorporated in a drive shaft provided with means for obtaining straight-line motion in an axial direction and means for obtaining rotational motion in a circumferential direction, and a portion below a lower end portion of said drive shaft is provided by a structure whereby the positional relationship between said laser projector of said double-walled tube accommodating said laser-transmission optical fiber and said objective portion of said double-walled tube accommodating said fiberscope is fixed;

external surfaces of said drive portions of said drive shaft, and said double-walled tube accommodating said laser-transmission optical fiber and said double-walled tube accommodating said fiberscope protruding from a lower end portion of said drive shaft, and penetration portions of said drive shaft through a case of said inspection machine have an airtight configuration; and surface shape of structural members inside said furnace are determined from distance data obtained by continuously scanning said laser beam over said surfaces.

2. The in-furnace inspection machine of claim 1, wherein said projected laser beam is a spot-shaped beam such that the light axis of said spot-shaped beam passes through the center of rotation of said drive shaft.

3. The in-furnace inspection machine of claim 1, wherein said projected laser beam is a slit-shaped beam forming a vertical surface such that a plane formed by said slit-shaped beam passes through the central axis of rotation of said drive shaft.

4. The in-furnace inspection machine of claim 1, wherein said fiberscope is incorporated with an irradiating light projector at an end thereof in said furnace and is configured integrally with a light guide connected to an irradiating light source arranged outside said furnace.

5. The in-furnace inspection machine of claim 1, wherein at least one assembly of a laser transmitting and projecting system and an image receiving and transmitting system is provided.

* * * * *